US012005239B2

(12) United States Patent
Dietschi et al.

(10) Patent No.: US 12,005,239 B2
(45) Date of Patent: Jun. 11, 2024

(54) EXTRUSION DEVICE AND COMPOSITE DELIVERY SYSTEM

(71) Applicant: EDELWEISS DR AG, Zug (CH)

(72) Inventors: Didier Dietschi, Geneva (CH); Beat Kilcher, Bosco Luganese (CH)

(73) Assignee: EDELWEISS DR AG (CH)

( * ) Notice: Subject to any disclaimer, the term of this patent is extended or adjusted under 35 U.S.C. 154(b) by 703 days.

(21) Appl. No.: 17/252,860

(22) PCT Filed: Jul. 2, 2019

(86) PCT No.: PCT/IB2019/055634
§ 371 (c)(1),
(2) Date: Dec. 16, 2020

(87) PCT Pub. No.: WO2020/008360
PCT Pub. Date: Jan. 9, 2020

(65) Prior Publication Data
US 2021/0154412 A1    May 27, 2021

(30) Foreign Application Priority Data
Jul. 2, 2018    (CH) .................................... 00825/18

(51) Int. Cl.
| A61M 5/315 | (2006.01) |
| A61C 5/64 | (2017.01) |
| A61M 5/44 | (2006.01) |
| B05C 17/01 | (2006.01) |
| B65D 83/00 | (2006.01) |

(52) U.S. Cl.
CPC .......... *A61M 5/31528* (2013.01); *A61C 5/64* (2017.02); *A61M 5/31511* (2013.01); *A61M 5/31586* (2013.01); *A61M 5/44* (2013.01); *B05C 17/0103* (2013.01); *B05C 17/0133* (2013.01); *B65D 83/0016* (2013.01); *A61M 2205/02* (2013.01); *A61M 2205/3673* (2013.01)

(58) Field of Classification Search
CPC .......... A61M 5/31528; A61M 5/31511; A61M 5/31586; A61M 5/44; A61M 2205/02; A61M 2205/3673; A61M 5/31581; A61C 5/64; A61C 5/62; B05C 17/0103; B05C 17/0133; B65D 83/0016; B65D 83/0011; A45D 40/04; A46B 11/0027
See application file for complete search history.

(56) References Cited

U.S. PATENT DOCUMENTS 3,156,387 A * 11/1964 Harwood ........... B65D 83/0011
401/175
4,074,833 A * 2/1978 Otto, Sr. ............ B65D 83/0011
222/390
(Continued)

FOREIGN PATENT DOCUMENTS

WO    WO 2011/023629    3/2011

*Primary Examiner* — Donnell A Long (57) ABSTRACT

A new type of syringe for delivering composite material for direct application of the material in the mouth of a patient. The new type of syringe includes a threaded screw for driving a piston through the syringe in order to extrude the material from the end of the syringe. The extrusion force is thus generated in the syringe, thereby allowing for a simpler, less costly motorised driving system using a torque driving movement. The syringe also includes a localised heating arrangement at the extrusion end.

19 Claims, 7 Drawing Sheets

(56) References Cited

U.S. PATENT DOCUMENTS

| | | | | | |
|---|---|---|---|---|---|
| 4,506,810 | A | * | 3/1985 | Goncalves | A45D 40/02 |
| | | | | | 222/391 |
| 4,544,083 | A | * | 10/1985 | Schroeder | A47J 9/00 |
| | | | | | 401/175 |
| 4,684,344 | A | | 8/1987 | Brockway | |
| 5,692,642 | A | * | 12/1997 | Brattesani | A61C 5/62 |
| | | | | | 221/199 |
| 5,795,337 | A | * | 8/1998 | Grimard | A61M 5/31511 |
| | | | | | 604/222 |
| 2003/0165793 | A1 | * | 9/2003 | Yobel | A61C 5/62 |
| | | | | | 433/32 |
| 2005/0178796 | A1 | * | 8/2005 | Shraiber | B65D 83/0011 |
| | | | | | 222/78 |
| 2006/0269893 | A1 | | 11/2006 | Aloise | |
| 2009/0191505 | A1 | | 7/2009 | Clark | |
| 2011/0117518 | A1 | * | 5/2011 | Pond | A61C 5/66 |
| | | | | | 433/89 |
| 2018/0250103 | A1 | * | 9/2018 | Pierson | B05C 17/0103 |
| 2021/0163212 | A1 | * | 6/2021 | Phipps | B65D 83/0022 |

* cited by examiner

EXTRUSION DEVICE AND COMPOSITE DELIVERY SYSTEM

The present invention relates generally to a syringe-type delivery device for viscous material, more particularly to a delivery system for a composite material such as those used in the field of dentistry.

The delivery of composite material for direct application of the material into the mouth of a patient has not changed over many decades. Known devices used for such delivery include the syringe, in which the material is extruded by turning a screw, and the compule, which is generally used in conjunction with a hand-activated gun to push the material through the compule.

Also known are motor-driven guns to push the material through the compule or through the syringe, however these generally require a sophisticated drive system, resulting in rather cumbersome designs in respect to the length of a system including the drive motor and syringe or compule. The existing motor-driven guns heat up substantially the entire syringe which triggers composite ageing and bears the limits of existing compule design and volume.

In view of the state of the art, certain advantages are met by providing a controlled motor-driven system for delivering composite material with a controlled flow. An electronically-controlled electric motor may be used. Advantages in limiting the amount of waste and in reducing the extrusion force requirements are achieved through modifying the viscosity of the material to be extruded. According to embodiments described herein, such modification may be achieved using a heating system applied to a precise region of the delivery system and the dispensing device.

According to the invention, there is provided a dispensing device, preferably with a pen-like shape, for delivering a composite material by extrusion via an extrusion channel provided at a first end of the device, the device comprising:
- a new capsule case, said extrusion channel being at a first end of the capsule case;
- a piston within the capsule case, the piston configured to be driven between a second end of the capsule case and the first end of the capsule case in a translational movement, a volume delimited between an inner face of the piston and the extrusion channel defining a chamber for holding the material for delivery; and
- a piston driving mechanism comprising a threaded screw, rotatable about an axis substantially coinciding with the translational motion of the piston, arranged such that rotation of the screw, at least in a first direction, engenders translation of the piston towards the first end of the capsule case.

According to the invention, a localized heating arrangement including a heating element is provided at an end of the delivery device case adjacent to the extrusion channel, the localized heating arrangement being configured to provide heat towards the extrusion channel of the dispensing device and also to a limited volume part of the chamber adjacent to the extrusion channel while avoiding or limiting the transfer of heat towards the main part of the chamber for holding the material for dispensing.

In an embodiment, an end part of the delivery device where the localized heating arrangement is provided is made from metal or from thermo-conductive plastics, whereas at least an adjacent part and possibly the remainder of the delivery device case is made of thermally insulating material.

In another embodiment, the heating element is a heating coil arranged in/or on a frusto-conical wall which joins a cylindrical outer wall of the chamber or of the delivery device case to the extrusion channel of smaller diameter. In a variation, a part of the heating coil is in/or on the frusto-conical wall, and another part of the heating coil extends into the extrusion channel.

According to this embodiment, the extrusion channel and the frusto-conical wall are both made of metal or of thermo-conductive plastics, optionally coated with a thermally insulated material, and at least an adjacent part of the cylindrical outer wall of the chamber is made of thermally insulating material.

Advantageously, in operation, material adjacent to the extrusion channel for extrusion via the extrusion channel is locally heated by the localized heating arrangement to a temperature at which the material has low viscosity, whereas material in the bulk of the chamber is relatively cool and viscous.

In another embodiment, the threaded screw extends into the chamber through a central hole in the piston, the piston comprising a sealing lip at the central hole, the sealing lip being made of a material which adaptably conforms to the profile of the threads of the screw, the piston arranged around the screw such that rotation of the screw directly drives said translational motion of the piston.

In this embodiment, the screw is preferably made from plastics and at least the sealing lip of the piston is made from a thermoplastic elastomer, also the thermoplastic elastomer is preferably moulded over the piston.

In this embodiment, the thread of the screw preferably has a trapezoidal profile and the sealing lip of the piston adaptably conforms to the trapezoidal profile of the thread of the screw also, the screw is arranged to extend a given distance into the chamber, the given distance being sufficient for the piston to be able to reach substantially the first end of the chamber.

In another embodiment, the threaded screw is located between the piston and the second end of the capsule case, the piston driving mechanism further comprising a nut having a threaded central hole through which the screw may pass, the nut configured such that at least a part of the nut urges against the piston to drive the piston towards the first end of the capsule case when the screw rotates at least in the first direction, at least part of the nut having an outer profile which conforms to the cross-sectional shape of the inner wall of the capsule case, thereby inhibiting rotational movement of the nut within the capsule case when the nut is driven.

Usually, the piston forms a tight fit against the inner wall of the chamber, thus inhibiting the material for delivery from passing between the piston and the inner wall of the chamber.

In another embodiment, said piston has a predetermined non-circular cross-sectional shape and said capsule case has an inner wall having a cross-sectional shape which conforms to the cross-sectional shape of the piston, thereby inhibiting rotational movement of the piston within the chamber during the translational motion of the piston when driven.

According to this embodiment, the matching cross-sectional profile of the inner wall of the chamber and the cross-sectional outer profile of the piston are of any of a polygon shape or an oval shape.

In another embodiment, at least an extremity part of the extrusion channel is provided with a thread on its outer surface for receiving an accessory attachment notably for attachments providing different extrusion forms, allowing for different anatomical configurations to be taken into consideration or for different material properties to be accounted for.

In all embodiments, the cartridge will preferably have a fixed length from the tip to the torque driver pin, whatever the composite volume in it, which allows the interchangeability of the cartridge at any moment without need to reposition the piston. This reduces significantly the operating time which is not the case with pistons moved by an external screw system.

In all embodiments, the capsule case preferably comprises a plurality of interchangeable cartridges of the same fixed length but different cartridges being of different volumes for containing different volumes of viscous composite materials to be extruded, interchangeability of the cartridges being achieved due to the uniform fixed length of the different cartridges.

According to a second aspect of the invention, there is provided a system for delivering a composite material by extrusion, the system comprising at least one dispensing device as defined previously and a driver unit;
the driver unit comprising a driver pin and motor unit to rotate the driver pin;
the screw of the dispensing device being configured to be driven by the driver pin of the driver unit;
the driver unit and the dispensing device being at least partly housed in a delivery device case;
the dispensing device and an inner surface of the delivery device case being arranged to be mutually coupled in a way which inhibits rotation, around the axis of rotation of the threaded screw, of the dispensing device and the delivery device case with respect to each other.

According to this second aspect, the driver unit further comprises a gear unit between the motor unit and the driver pin.

The present invention and its advantages will be better understood with reference to the enclosed drawings and to the detailed description of various embodiments, wherein.

There is disclosed a device and a system for delivering a composite material for direct application to the mouth of a patient. The device and system may find use in the field of dentistry. More generally, a composite material can be any viscous material which can be extruded from a compule or syringe. Preferably, the composite material is delivered by extrusion via an extrusion channel of the syringe or compule.

Figure 1:
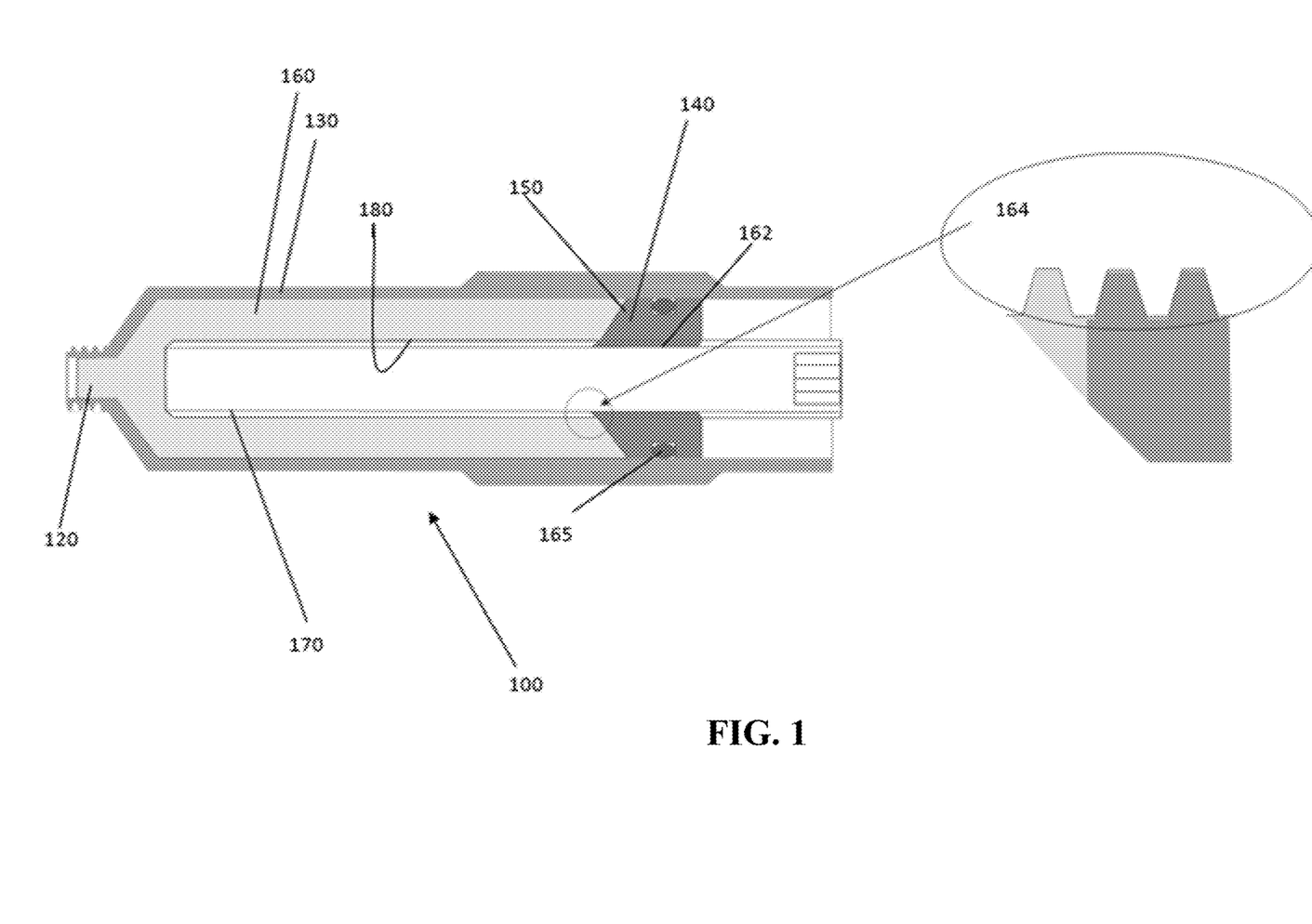
FIG. 1 shows an embodiment of a dispensing device described herein.

FIG. 1 shows a new syringe assembly according to an embodiment of the present invention. In more general terms, a dispensing device 100 is provided, having a capsule in which a material to be delivered by extrusion may be held. The capsule has a case 130, with a channel 120 at one end through which the material may be extruded. Within the capsule is a piston 140 for pushing the composite through the chamber 160 of the capsule, where the composite is held. The chamber 160 may be defined as volume defined by the inner wall of the capsule 180 between the extrusion channel 120 and the inner face 150 of the piston 140. The piston is configured to be pushed between a second end of the capsule and the first end where the extrusion channel is located. By pushing the piston from the second end towards the first end, this causes the material to be pushed out of the device through the extrusion channel at the first end. In the embodiment illustrated in FIG. 1, the piston has a central hole 162 through which a screw 170 passes. The screw has a thread so that when the screw is rotated in a given direction, the piston, which cooperates with the screw, is pushed along the length of the chamber, which in turn pushed the material towards the extrusion channel and out of the device. According to an embodiment, the screw may be turned by an electric motor. Turning the screw in the opposite direction causes the piston to travel laterally through the chamber in the opposite direction. In order for the piston to be able to slide through the chamber as a result of the screw turning, the piston must not rotate within the chamber. The rotational motion of the screw is transformed to the translational motion of the piston.

The extrusion of the capsule case end is preferably, in accordance with the invention, provided with a localized heating arrangement as will be described in detail later. This has the advantage that, in operation, material adjacent to the extrusion channel for extrusion via the extrusion channel is locally heated by the localized heating arrangement to a temperature at which the material has low viscosity, whereas material in the bulk of the chamber is relatively cool and viscous, as will also be described in detail later.

The piston and the screw preferably have a tight fit between each other so that the material is pushed efficiently through the chamber. According to an embodiment, the screw is made from plastics material and at least the centre part of the piston, through which the screw projects, is made from a resilient material in order to be able to follow the contour of the thread of the screw as the piston slides along the length of the chamber, without rotating within the chamber. According to an embodiment, the screw thread has a trapezoidal profile and the piston is made from a thermoplastic material. According to an embodiment, the piston is made from a thermoplastic elastomer material, which is moulded over the piston in order that the shape of the hole through the piston may adapt without clearance to the trapezoidal profile of the screw thread as it travels through the piston. The material with which at least the central part of the piston is formed allows this part of the piston to adaptively conform to the profile of the thread of the screw. The piston may be fitted with an O-ring 165 to provide a seal against the inner wall of the capsule.

FIG. 1 shows a expanded detailed image of the piston near the hole where the screw passes through. The conforming nature of the material of the piston around the hole allows this part of the piston to follow the profile of the thread of the screw, thus providing a seal and also ensuring that the material to be extruded is removed from the screw threads. This part of the piston may therefore be described as a lip 164. The lip adaptably conforms to the profile of the thread of the screw during the travel of the piston through the chamber and of the screw through the piston.

According to an embodiment, the thread may have a trapezoidal profile. When the screw passes through the piston, the lips therefore also adopt a trapezoidal form, as shown in FIG. 1. This form continually adapts as the screw travels through the piston, allowing the lips of the piston to closely follow the profile of the thread of the screw.

Figure 2A:
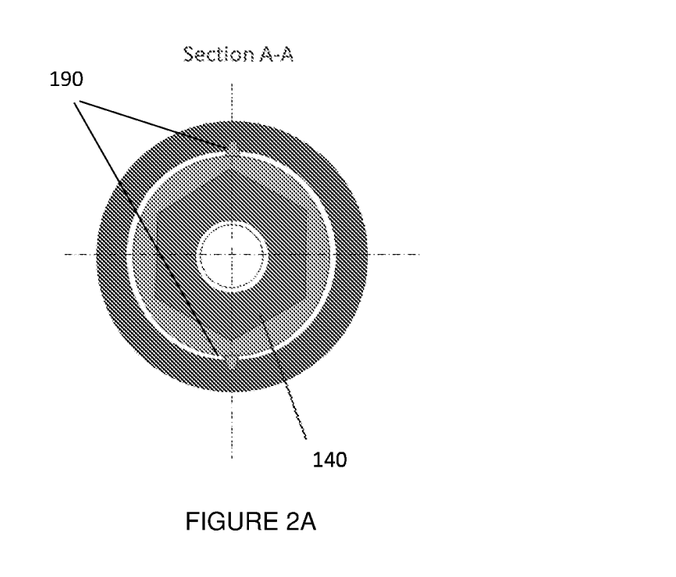
FIG. 2a shows a cross-sectional view along an axis of a capsule of the dispensing device of FIG. 1, where a piston and a screw can be seen.
Figure 2B:
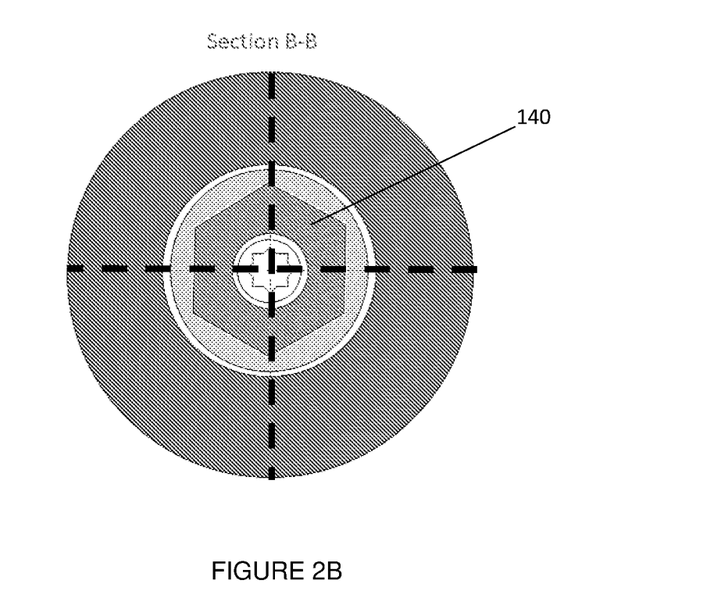
FIG. 2b shows a cross-sectional view along an axis of another part of the capsule of the dispensing device of FIG. 1, where the piston, a screw and part of a driver connector mechanism can be seen.
Figure 6A:
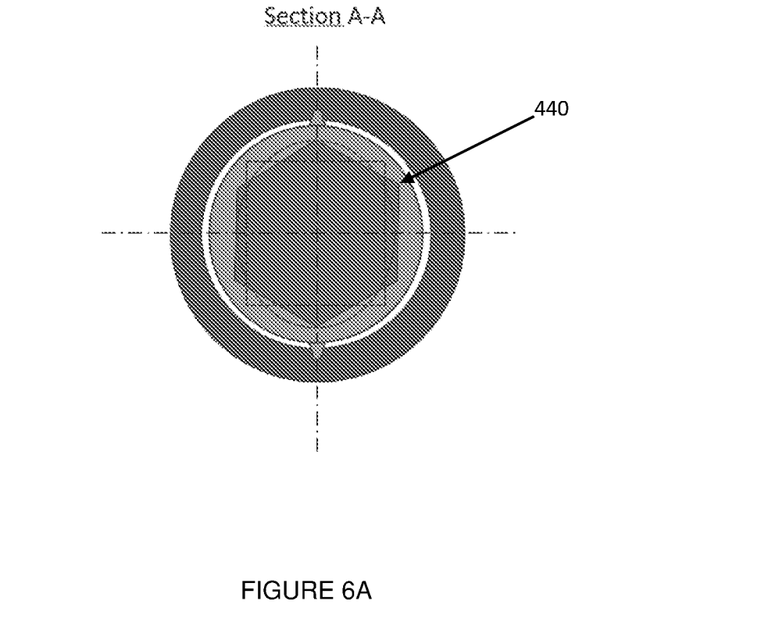
FIG. 6a shows a cross-sectional view along an axis of another embodiment of the capsule of the dispensing device of FIG. 4, where the piston can be seen.
Figure 6B:
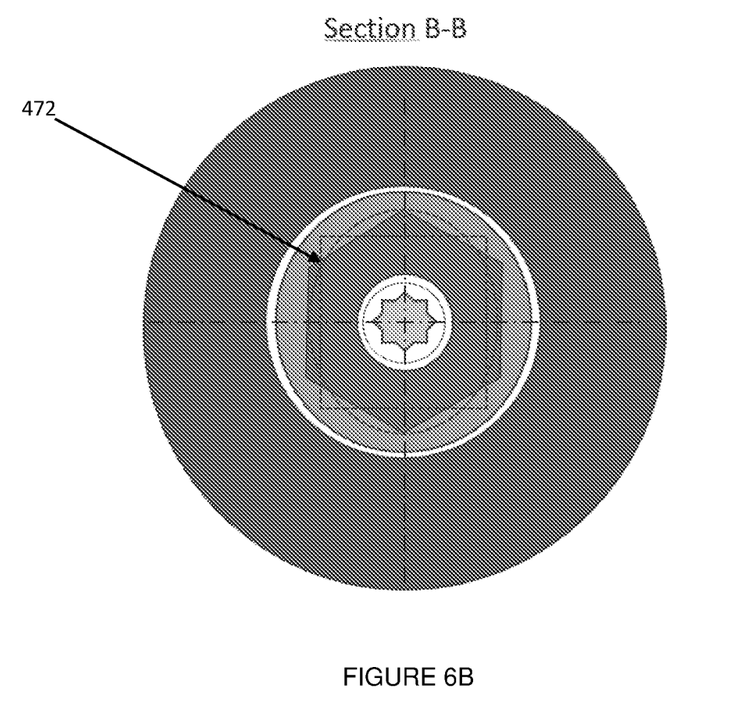
FIG. 6b shows a cross-sectional view along an axis of the capsule of another embodiment of the dispensing device of FIG. 4, where the piston, the screw and part of a driver connector mechanism can be seen.

In order to prevent the piston from rotating within the chamber, the inner wall of the capsule has a different cross-sectional shape from the capsule's outer case, which may be cylindrical. Moreover, the cross-sectional shape of the inner wall of the capsule preferably matches the cross-sectional shape of the piston. According to an embodiment, the cross-sectional shape of the chamber is the same as the cross-sectional shape of the outer edge of the piston, with the piston fitting tightly within the chamber in order to prevent the material to be extruded from flowing back behind the piston. FIG. 1 and FIGS. 2*a* and 2*b* show pistons and chamber walls having a hexagonal shape. Other shapes are suitable, for example a square or any other polygon shape. Oval shapes are also suitable because all of these shapes prevent the rotational movement of the piston within the chamber as the piston is pushed along the length of the chamber by the rotation of the screw. Any shape which prevents the piston from twisting within a capsule whose inner wall follows the same shape as the piston is suitable. Consequently, a circle shape is not suitable because it would not prevent the piston from twisting due to the rotational force exerted on the screw in order to move the piston. The dotted lines shown in FIGS. 6*a* and 6*b* illustrate a number of examples of suitable piston shapes and capsule inner profiles which can be used, as well as the hexagon shape, which is shown in bold line.

Figure 3:
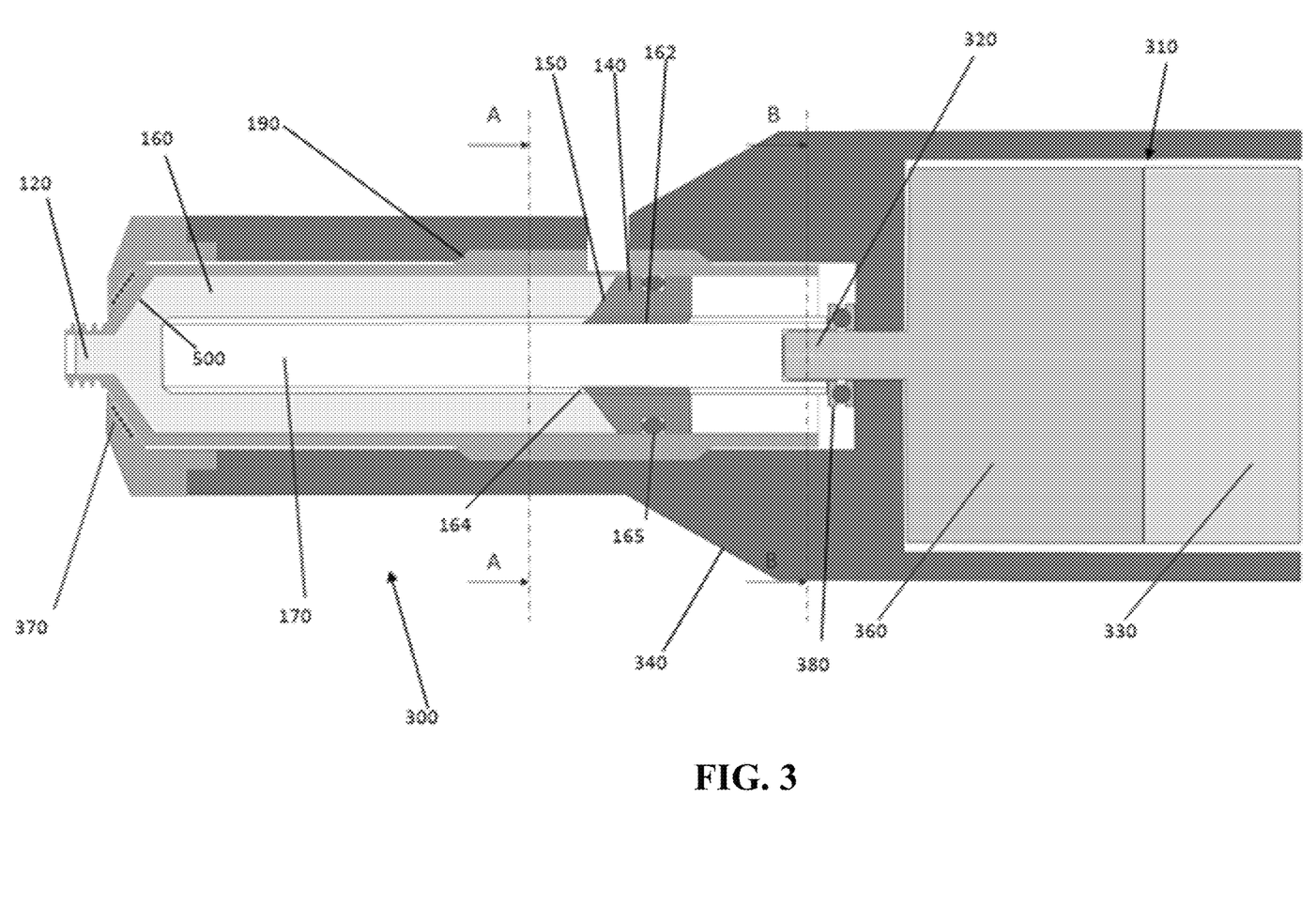
FIG. 3 shows a side view of a system comprising a delivery device and the dispensing device of FIG. 1.

The back end of the screw, which is to be driven, preferably by a motor for turning the screw, is provided with a connecting mechanism to allow the screw to be coupled to a motor. Suitable connecting mechanisms include a profiled recess into which a corresponding profiled pin may be inserted. FIG. 2*b* shows a recess having a multi-pointed star shape, for example. FIG. 3 shows a driver pin 320 engaging with the profiled recess in the screw.

FIG. 3 shows an embodiment of a system according to an embodiment of the present invention. The system 300 comprises a syringe or dispensing device 100 as described above, and a driver unit, both being housed in a delivery device case. A locking system 190 is arranged in order to prevent the dispensing device from twisting within the case when the screw of the dispensing device is turned or when an attachment accessory is screwed onto the end of the extrusion channel. The end of the screw 170 which extends towards the exterior of the dispensing device, at its second end, is configured to interlock with a driver pin of a motor unit 330 for driving the screw. The driver unit 310 includes the motor unit 330 and the driving pin, driven by the motor unit. During operation, the motor 330 turns the driving pin 320, which in turn causes the screw 170 with which it is engaged to be driven. The turning screw causes the piston, which is blocked from rotation due to its shape and the corresponding shape of the inner part of the capsule, to slide along the inside of the capsule. The motor unit may be supplied by an external power source or the motor unit may comprise a battery power source. An optional gear unit 360 may be arranged between the motor unit and the driving pin.

According to an embodiment, the delivery device may comprise an axial stop to prevent axial forces being transferred from the moving piston towards the driver unit. A suitable axial stop could be a bearing which is free to rotate around the axis of the driving pin. When the driving pin turns, it generates torque for transferring rotational forces to the screw. The turning screw causes the piston to move, axial to the turning screw. Hence, an axial force is exerted on the piston in one direction and the resulting reaction force is generated in the opposite direction, towards the driving pin. Advantageously, it should be avoided that any of these axial forces be transmitted to the motor unit or to the gear unit. The delivery device may therefore include an axial stop 380 to control the axial forces. The axial stop may be a bearing, for example a ball bearing, allowing the axial stop to rotate freely around the axis of the driving pin. Thus, the axial stop may generate a reaction in the opposite direction to the reaction of the moving piston, thereby transmitting an action on the delivery device case rather than on the driving pin, thanks to the low radial force of the axial stop. Thanks to the axial stop, torque can be transferred by the driver pin without axial forces being transferred to the motor unit or the gear unit.

The first end of the delivery device may be opened, using a screw system or a bayonet system, for example, to allow the dispensing device to be removed. Any other suitable system may be used to allow the removal of the syringe, such as a flap on the side of the delivery device case. The end of the delivery device includes a heating element 370 for heating a small part of the material to be extruded. Further discussion for this is provided below.

Figure 4:
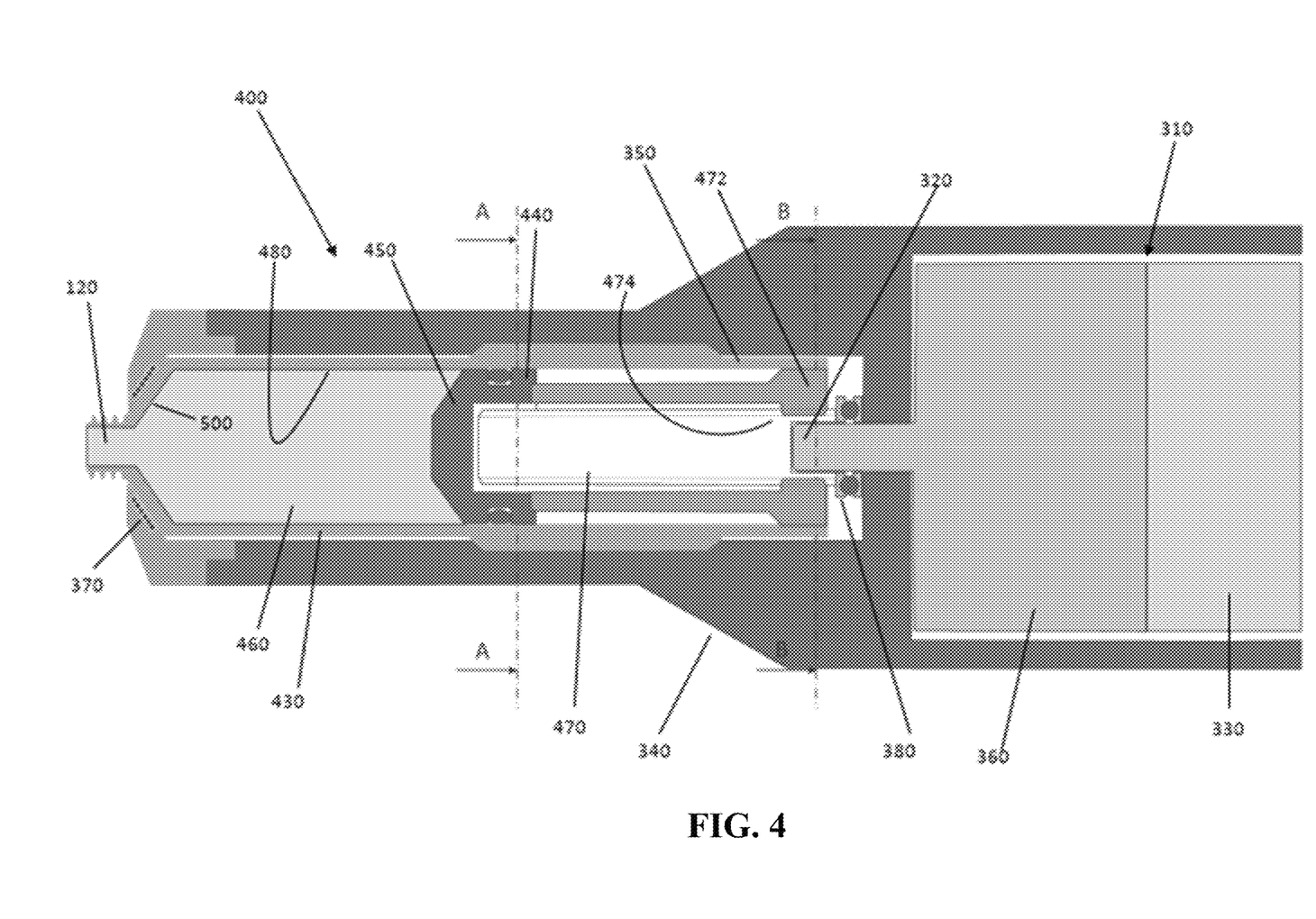
FIG. 4 shows a dispensing device according to another embodiment described herein, the dispensing device placed within the delivery device of FIG. 3.

FIG. 4 shows a different embodiment of a system according to the present invention. In this embodiment, the driver unit 310 may be the same as the one of FIG. 3 and the system may be housed in the same delivery device case 340 as that of FIG. 3. In fact, for all intents and purposes, the system of the embodiment of FIG. 4 may look aesthetically exactly the same as that of FIG. 3 from the user's point of view. The difference is in the design of the syringe or dispensing device. The dispensing device of FIG. 4 differs from that of FIG. 3 in that the screw does not go through the piston and so the screw does not extend into the chamber where the material for delivery is held. Consequently, the screw does not always have to be as long as the one of FIG. 3, the length of which allows the piston to reach the first end of the chamber where the extrusion channel lies. The piston of the embodiment of FIG. 4 does not require the lip shown in FIG. 3 because there is no hole in the piston for the screw and so the whole inner face of the piston is used to push the composite. The back of the piston requires, at most, a blind hole just to receive a part of the screw. In other embodiments, the piston does not even have a blind hole. The screw is not even required to touch the back of the piston. Instead, it is arranged for a nut to perform the function that the piston with its resilient lip of FIG. 3 performs. The nut 472 is located behind the piston and the screw thread goes through the nut. A prolongation of the nut or any other piece, such as an extension washer, may be used to cause the nut to push against the back of the piston to make it move through the chamber. In this embodiment, the cross-sectional form of the piston follows that of the inner wall of the chamber in order that the piston may efficiently push all or at least most of the material through the chamber. The cross-sectional form of the nut should also match that of the inside of the chamber because this prevents the nut from rotating when the screw rotates and causes the nut, and therefore the piston, to travel in a longitudinal direction towards the extrusion channel.

Figure 5A:
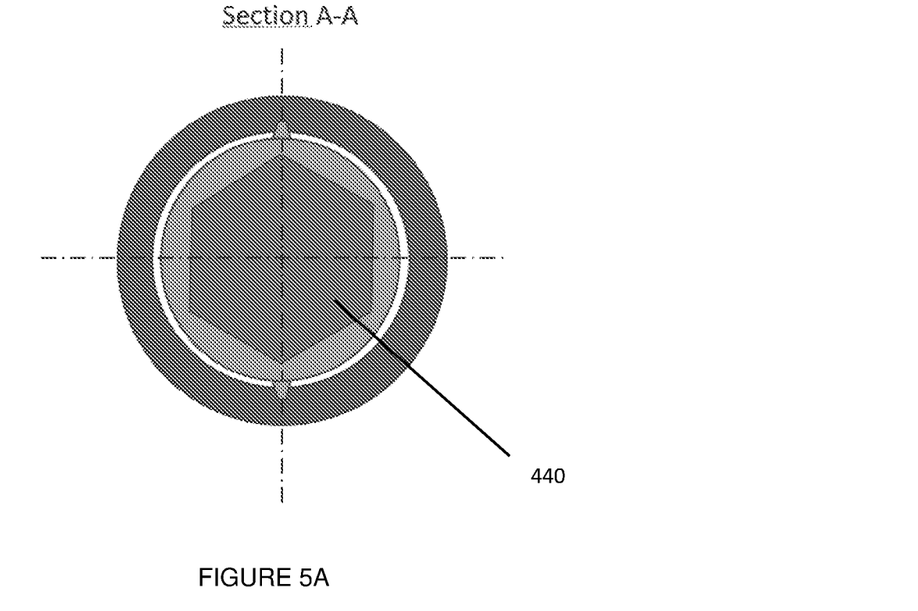
FIG. 5a shows a cross-sectional view along an axis of the capsule of the dispensing device of FIG. 4, where the piston can be seen.
Figure 5B:
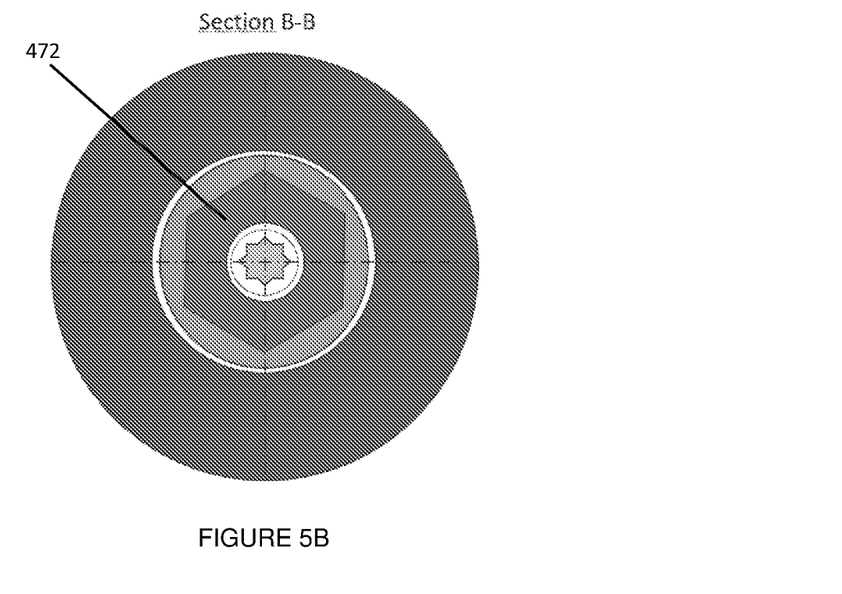
FIG. 5b shows a cross-sectional view along an axis of the capsule of the dispensing device of FIG. 4, where the piston, the screw and part of a driver connector mechanism can be seen.

FIG. 5a is a frontal, cross-sectional view of the piston and the chamber of the embodiment shown in FIG. 4. In this view, the screw is not visible as it is in FIG. 2a because it stays behind the piston, without passing through it. FIG. 5b is essentially the same as FIG. 2b on the other hand.

FIG. 6a shows a cross-sectional view along an axis of another embodiment of the capsule of the dispensing device of FIG. 4, where the piston can be seen and FIG. 6b shows a cross-sectional view along an axis of the capsule of another embodiment of the dispensing device of FIG. 4, where the piston, the screw and part of a driver connector mechanism can be seen.

Figure 7:
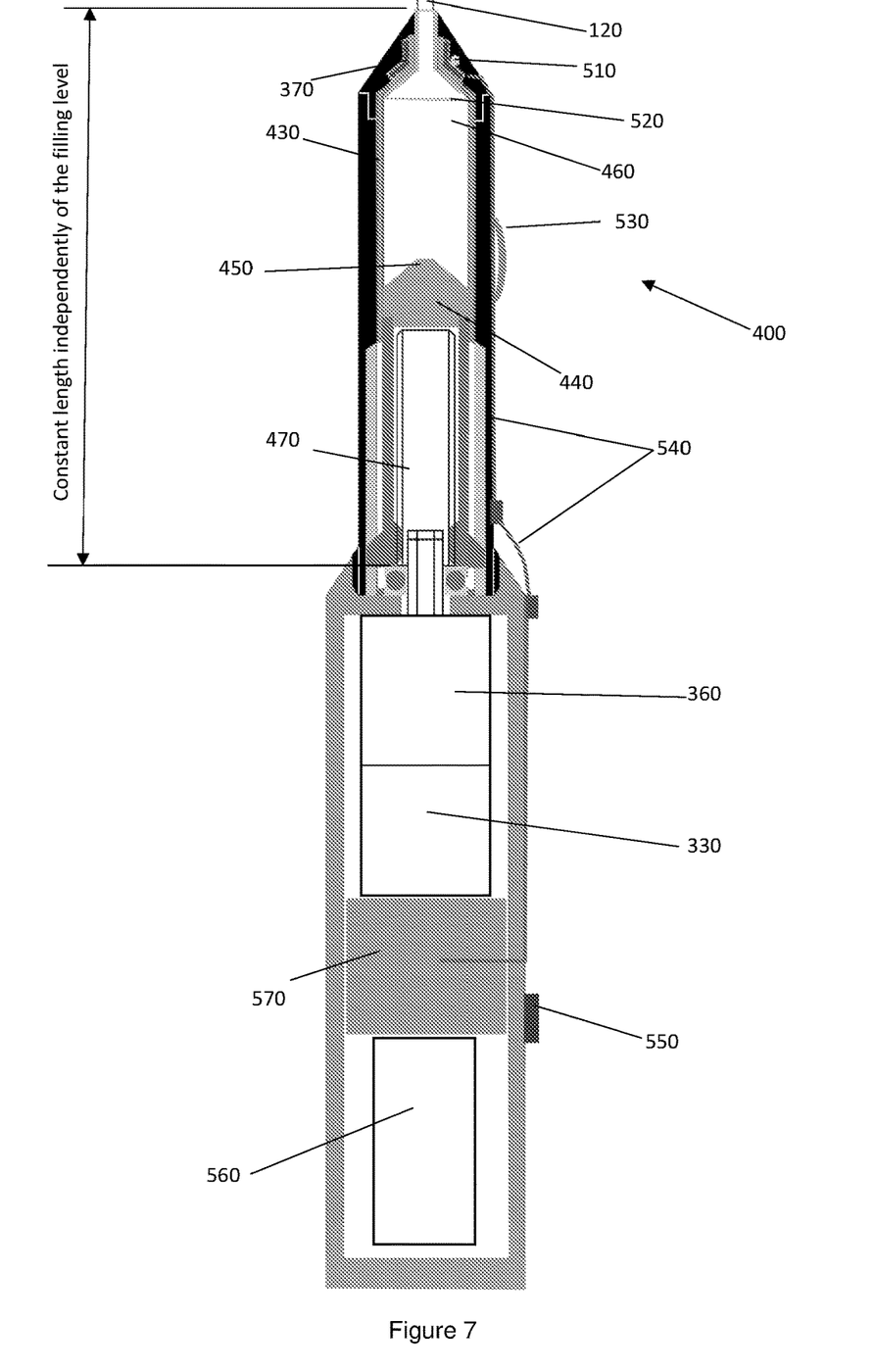
FIG. 7 shows a cross-sectional view along an axis of the capsule of another embodiment of the dispensing device with a modified localized heating arrangement.

FIG. 7 illustrates a modified localized heating arrangement. As shown in FIG. 7, a dispensing device 400 delivers a composite material by extrusion via an extrusion channel 120 provided at a first end of the device. The device comprises a capsule case 430, said extrusion channel being at a first end of the capsule case. The device also comprises a piston 440 within the capsule case, the piston configured to be driven between a second end of the capsule case and the first end of the capsule case in a translational movement, a volume delimited between an inner face 450 of the piston and the extrusion channel defining a chamber 460 for holding the material for delivery. Furthermore, the device comprises a piston driving mechanism comprising a threaded screw 470, rotatable about an axis substantially coinciding with the translational motion of the piston, arranged such that rotation of the screw, at least in a first direction, engenders translation of the piston towards the first end of the capsule case.

A localized heating arrangement including a heating element 370 is provided at an end of the delivery device case 430 adjacent to the extrusion channel 120. The localized heating arrangement is configured to provide heat towards the extrusion channel 120 of the dispensing device and also to a limited volume part of the chamber 460 adjacent to the extrusion channel 120 while avoiding or limiting the transfer of heat towards the main part of the chamber 460 for holding the material for dispensing.

For this purpose, the heating element 370 is a heating coil that has a first part arranged on a frusto-conical part of an internal metal funnel 520 made for example of inox and a second part that extends into the extrusion channel partly over the narrow cylindrical extension of the funnel. This inclined first part of the heating coil directs heat into a limited volume of the composite material in the chamber 460 adjacent to the extrusion channel 120, whereas the rectilinear second part of the heating coil heats the extruded composite material passing through the extrusion channel. Both parts of the heating coil are attached inside to the funnel 520 by a thermally conductive material, whereas on the outside they are covered by a thermally insulating material. Embedded in this thermally insulating material is a temperature sensor 510.

The system includes an electronic control module 570 for sensing and precisely controlling the temperature at the end of the delivery device case where the extrusion channel is located, wherein the temperature sensor 510 is arranged. By precise control of the temperature at this part, it is possible to maintain the optimum temperature and optimum viscosity of the material being extruded.

The device illustrated comprises a flat switch 530 for composite extrusion and a dip switch 550 for setting heating temperature.

The device also comprises a compartment within a part of the case for housing batteries 560 for the motors.

All of the embodiments of the system allow for a simplified driver unit design because the screw/nut/piston configurations are built into the syringe. In the embodiment of FIG. 3, the piston can be said to serve the function of both the piston and the nut of the embodiment of FIG. 4.

All of the embodiments described herein allow for the delivery of a composite or otherwise viscous material in a controlled flow using a motorised driving system. The shape of the composite at the delivery point may be controlled through appropriate shaping of the extrusion channel and further shaping and precision of delivery may be achieved through the use of interchangeable detachable tips which may be screwed onto the external thread located on the outer surface of at least part of the extrusion channel. The tips may have various sizes, shapes and angles in order to achieve the desired size and shape of material to be delivered and various designs are possible to allow the composite to be delivered to places within a patient's mouth which would otherwise be difficult to reach.

Disposable interchangeable tips allow for minimising of cross contamination. Loss of material may be achieved through precisely controlled driving of the piston through the chamber. The system may include a gear unit 360 between the motor unit and the driving pin to help achieve precise control of the rotation of the screw. Preferably, the gear unit may be located in the delivery device case. Fine-pitch threads may be selected for the screw in order to achieve accurately controlled piston displacement and therefore to limit the loss of material.

Many different types of composite materials are known in the field of dentistry. Different types of composite materials have different viscosities. Runnier, or less viscous materials are easier to extrude than more viscous materials and the resulting force required to extrude a less viscous material may be significantly less than for a more viscous material. When less force is needed, a smaller motor may be used to extrude the material from a syringe or a compule, and the resulting extrusion system or device may be more compact and easy to manipulate. By heating a viscous material, it is often possible to render the material less viscous. Instead of heating the whole capsule full of material to make it less viscous, according to the invention, heat is applied to the part of the material located at or near the extrusion chamber where the restricted opening size, compared with the rest of the capsule, may cause a more viscous material to get blocked. By heating this part of the material only, the viscosity can be sufficiently reduced to allow the material to be extruded with less force. Additionally, for delivery device cases which are less thermally resistive, having all of the material at a high temperature would be uncomfortable for the user. According to the invention, the delivery device case has a localized heating arrangement or ring at its nose, where the end of the capsule having the extrusion channel lies. Heat from the heating ring is transferred to the extrusion channel and the vicinity thus causing a part of the material in the chamber to heat up. This front part of the delivery device casing may be made from a material which transfers heat efficiently, such as a metal or a thermo-conductive plastic material, while the rest of the delivery device case may be made from a thermally insulating material thus allowing the device to be comfortable to handle for the user.

According to an embodiment, the system includes a control module for sensing and precisely controlling the temperature at the end of the delivery device case where the extrusion channel is located. By precise control of the temperature at this part, it is possible to maintain the optimum temperature and optimum viscosity of the material being extruded.

According to yet another embodiment of the present invention, the delivery device case may comprise two dispensing devices. This embodiment is useful for procedures in which two separate composite materials are to be applied, which may often be the case in the field of dentistry. For example, one composite material could be an enamel while the other could be a dentine. Each dispensing device has its own specially shaped piston, screw and capsule case and its own piston-driving mechanism. Consequently, the delivery device case houses two motors, one to turn each screw. According to a first variant, the system may be provided with an electrical cable, for example at the back of the delivery case, for providing power to the motors, preferably located within the case. In other embodiments a compartment within a part of the case may house batteries for the motors. The compartment may also include a temperature controller. The heating ring or heating element, where present, is arranged in the delivery device case towards the end where the extrusion channels of the dispensing devices are designed to lie. The heating element may be a single element whose layout is designed to efficiently transfer heat towards the end of the extrusions channel(s) either one or both of the dispensing devices. Alternatively, in embodiments in which advantage is to be gained through providing heat towards the ends of the extrusion channels of both dispensing device, the heating element may comprise a plurality of parts, arranged in such a way as to transfer the heat efficiently to the desired areas. In embodiments in which the speed of rotation of the screws may be controlled, the compartment may house a motor speed controller, which may include a gear unit. Any of the modules for the embodiments and variants mentioned here may also be used for the one-motor versions of any of the other embodiments mentioned previously.

Any of the embodiments may be used with a charger device, preferably located in a charging base on which the system may rest when not being used.

In order to prevent the syringe or dispensing device from twisting within the delivery device case, all embodiments preferably feature an anti-twist mechanism 190. FIG. 2a shows an example of an anti-twist mechanism, where the dispensing device has a raised portion along its length, which fits into a corresponding groove in the inner wall of the chamber of the capsule. FIG. 1 shows the raised portion of the dispensing device. Any other anti-twist stabilisation system can be used as long as it blocks the dispensing device in a fixed place and prevents or otherwise inhibits a twisting motion of the dispensing device within the delivery device case during operation. The delivery device case may be opened up to allow the dispensing device to be removed and exchanged.

Syringes according to embodiments described herein may have external dimensions compatible with known syringes, such as 1 ml syringes or 3-5 g syringes. Moreover, the syringes have a generally pen-like shape.

Embodiments of the present invention allow for the extrusion of a composite material from the extrusion channel by torque action driving of one end of a capsule in which the material is held. This allows for a simpler driver unit to be used compared to a system which requires axial force for the extrusion. The resulting system can therefore be more compact, less costly, giving a more ergonomic design. A prefilled syringe according to an embodiment may be mounted into the delivery device case, where its screw may be engaged with the driving pin of the driver unit.

Dispensing devices according to embodiments of the present invention may be provided with a thread on the outer surface of at least the extremity of the extrusion channel. This allows for an accessory to be attached to the end of the extrusion channel by a screwing motion. The accessory may be a tip, specially formed, preferably by appropriate design of the size and shape of an opening at the end of the tip, among others, to deliver the composite material with a particular thickness or increment shape. An increment shape may be any shape whose profile increments as the composite is deposited. Different tips may be screwed onto the extrusion channel, allowing for different anatomical configurations to be taken into consideration or for different material properties to be accounted for. This feature allows for small quantities of the composite to be delivered incrementally, thus allowing for the appropriate anatomical profile to be achieved. This is a new feature in composite application. A further improvement brought about by embodiments of the present invention is that it helps to avoid possible cross contamination, which is a potential problem with known disposable tips. The system includes means to prevent the syringe from twisting when it is held in the delivery device case, thus facilitating the screwing on and/or off of the different tips.

The screw rotates inside the syringe, thus causing the piston to move in the direction of the extrusion channel. The viscosity of the material is altered through heating close to the extrusion channel, thus allowing a lower extrusion force to be applied and the benefits which follow. An elastic removal lip is mounted on the piston of embodiments in which the screw passes through the piston. Once the piston has extruded all the composite, a new one can be inserted.

More accurate and dynamic composite delivery is achievable because the extrusion force is generated within the syringe and not outside as with prior art designs. Aging of the composite is avoided through heating of the composite at the extrusion channel because it reduces the viscosity of the material and allows it to be extruded with less force, especially when the material is of a particularly high viscosity. Lower viscosity also helps during application and modelling during cavity filling is rendered easier. A thread on the syringe allows to adapt the extrusion string in different shapes, such as round, rectangular like, etc, according to the dentist's needs.

In all embodiments, the cartridge will preferably have a fixed length from the tip to the torque driver pin, whatever the composite volume in it, which allows the interchangeability of the cartridge at any moment without need to reposition the piston. This reduces significantly the operating time which is not the case with pistons moved by an external screw system.

This functionality is important if a dentist is using one dispensing device and during the composite application he has to change from e.g. a dentine composite to e.g. an enamel composite. The fact that the external screw system has to be removed from the inside of the syringe and be repositioned with the exchanged syringe, because the piston is always in a different position, appreciably increases the wasted time. In addition, the integrated solution with exchangeable cartridges permits to simplify the driving system, because there is no need for fast and slow movement functionalities of the driver system with e.g. a more complicated spur gear but it's possible to use a slow speed driving system with high torque without losing time during syringe exchange.

The claimed localized heating arrangement is particularly advantageous but it is also possible to provide a dispensing device with the other described features with no localized heating arrangement.

The invention claimed is:

1. A dispensing device (100, 400) for delivering a composite material by extrusion via an extrusion channel (120) provided at a first end of the dispensing device (100, 400), the dispensing device (100, 400) being configured to be housed in a delivery device case (340), the dispensing device (100, 400) comprising:
   a capsule case (130, 430), said extrusion channel (120) being at a first end of the capsule case (130, 430);
   a piston (140, 440) within the capsule case (130, 430), the piston (140, 440) configured to be driven between a second end of the capsule case (130, 430) and the first end of the capsule case (130, 430) in a translational movement, a volume delimited between an inner face (150, 450) of the piston (140, 440) and the extrusion channel (120) defining a chamber (160, 460) for holding the composite material for delivery;
   a piston driving mechanism comprising a threaded screw (170, 470), rotatable about an axis substantially coinciding with the translational motion of the piston (140, 440), arranged such that rotation of the threaded screw (170, 470), at least in a first direction, engenders translation of the piston (140, 440) towards the first end of the capsule case (130, 430); and
   a localized heating arrangement including a heating element (370) being provided at an end of the delivery device case (340) adjacent to the extrusion channel (120) for heating the composite material;
   wherein,
   a cylindrical outer wall of the chamber (160, 460) or of the delivery device case (340) of a larger diameter is extended by the extrusion channel (120) which is coaxial with the cylindrical outer wall of the chamber (160, 460) and is of a smaller diameter, and the cylindrical outer wall of the chamber (160, 460) or of the delivery device case (340) is joined to the coaxial extrusion channel (120) of the smaller diameter by a frusto-conical wall (500) forming a funnel (520);
   the localized heating arrangement is configured to provide heat towards the extrusion channel (120) of the dispensing device (100, 400) and also to a limited volume part of the chamber (160, 460) adjacent to the extrusion channel (120) while avoiding or limiting the transfer of heat towards a main part of the chamber (160, 460) for holding the composite material for dispensing; and
   the heating element (370) is a heating coil comprising an inclined part arranged in or on the frusto-conical wall (500), the inclined part of the heating coil directing heat into said limited volume part of the chamber (160, 460) adjacent to the extrusion channel (120), whereas another part of the heating coil extends around the extrusion channel (120) for heating the extruded composite material passing through the extrusion channel (120).

2. The dispensing device (100) according to claim 1, wherein an end part of the delivery device case (340) where the localized heating arrangement is provided is made from metal or from thermo-conductive plastics, optionally covered with a thermally insulated material, whereas at least a part adjacent to the end part of the delivery device case (340) is made of thermally insulating material.

3. The dispensing device (100, 400) according to claim 1, wherein the extrusion channel (120) and the frusto-conical wall (500) are both made of metal or of thermo-conductive plastics, optionally covered with a thermally insulating material, and at least an adjacent part of the cylindrical outer wall of the chamber (160, 460) is made of thermally insulating material.

4. The dispensing device (100, 400) according to claim 1, wherein, in operation, the composite material adjacent to the extrusion channel (120) for extrusion via the extrusion channel (120) is locally heated by the localized heating arrangement to a temperature at which the material has low viscosity, whereas the composite material in a bulk of the chamber (160,460) is relatively cool and viscous.

5. The dispensing device (100, 400) according to claim 1, wherein the threaded screw (170, 470) extends into the chamber (160, 460) through a central hole (162) in the piston (140, 440), the piston (140, 440) comprising a sealing lip (164) at the central hole (162), the sealing lip (164) being made of a material which adaptably conforms to the profile of the threads of the screw (170, 470), the piston (140, 440) arranged around the threaded screw (170, 470) such that rotation of the threaded screw (170, 470) directly drives said translational motion of the piston (140, 440).

6. The dispensing device (100, 400) according to claim 5, wherein the threaded screw (170, 470) is made from plastics and at least the sealing lip (164) of the piston (140, 440) is made from a thermoplastic elastomer.

7. The dispensing device (100, 400) according to claim 6, wherein the thermoplastic elastomer is moulded over the piston (140, 440).

8. The dispensing device (100, 400) according to claim 5, wherein the thread of the screw (170, 470) has a trapezoidal profile and the sealing lip (164) of the piston (140, 440) adaptably conforms to the trapezoidal profile of the thread of the screw (170, 470).

9. The dispensing device (100, 400) according to claim 5, wherein the threaded screw (170, 470) is arranged to extend a given distance into the chamber (160, 460), the given distance being sufficient for the piston (140, 440) to be able to reach substantially the first end of the chamber (160, 460).

10. The dispensing device (100, 400) according to claim 1, wherein the threaded screw (170, 470) is located between the piston (140, 440) and the second end of the capsule case (130, 430), the piston driving mechanism further comprising a nut (472) having a threaded central hole (474) through which the threaded screw (170, 470) may pass, the nut (472) is configured such that at least a part of the nut (472) urges against the piston (140, 440) to drive the piston (140, 440) towards the first end of the capsule case (130, 430) when the threaded screw (170, 470) rotates at least in the first direction, at least part of the nut (472) having an outer profile which conforms to the cross-sectional shape of the inner wall (480) of the capsule case (130, 430), thereby inhibiting rotational movement of the nut (472) within the capsule case (130, 430) when the nut (472) is driven.

11. The dispensing device (100, 400) according to claim 1, wherein the piston (140, 440) forms a tight fit against the inner wall (480) of the chamber (160, 460), thus inhibiting the composite material for delivery from passing between the piston (140, 440) and the inner wall of the chamber (160, 460).

12. The dispensing device (100, 400) according to claim 1, wherein said piston (140, 440) has a predetermined non circular cross-sectional shape and said capsule case (130, 430) has an inner wall (180, 480) having a cross-sectional shape which conforms to the cross-sectional shape of the piston (140, 440), thereby inhibiting rotational movement of the piston (140, 440) within the chamber 060, 460) during the translational motion of the piston (140, 440) when driven.

13. The dispensing device (100, 400) according to claim 12, wherein the matching cross-sectional profile of the inner wall (180, 480) of the chamber (160, 460) and the cross-sectional outer profile of the piston (140, 440) are of any of a polygon shape or an oval shape.

14. The dispensing device (100, 400) according to claim 1, wherein at least an extremity part of the extrusion channel (120) is provided with a thread on its outer surface for receiving an accessory attachment.

15. A system (300) for delivering a composite material by extrusion, the system (300) comprising at least one dispensing device (100, 400) according to claim 1 and a driver unit (310);
the driver unit (310) comprising a driver pin (320) and motor unit (330) to rotate the driver pin (320);
the threaded screw (170, 470) of the dispensing device (100, 400) being configured to be driven by the driver pin (320) of the driver unit (310);
the driver unit (310) and the dispensing device (100, 400) being at least partly housed in the delivery device case (340);
the dispensing device (100, 400) and an inner surface (350) of the delivery device case (340) being arranged to be mutually coupled in a way which inhibits rotation, around the axis of rotation of the threaded screw (170, 470), of the dispensing device (100, 400) and the delivery device case (340) with respect to each other.

16. The system (300) according to claim 15, wherein the driver unit (310) further comprises a gear unit (360) between the motor unit (330) and the driver pin (320).

17. The system (300) according to claim 15, further comprising a temperature control unit for controlling the temperature at an extrusion channel end of the dispensing device (100, 400).

18. The dispensing device according to claim 1, wherein the capsule case (130, 430) comprises a plurality of interchangeable cartridges of the same fixed length but different cartridges being of different volumes for containing different volumes of viscous composite materials to be extruded, interchangeability of the cartridges being achieved due to the uniform fixed length of the different cartridges.

19. The dispensing device according to claim 1, wherein an end part of the delivery device case (340) where the localized heating arrangement is provided is made from metal or from thermo-conductive plastics, optionally covered with a thermally insulated material, wherein a part adjacent to the end part of the delivery device case (340) and the remainder of the delivery device case (340) are made of thermally insulating material.

\* \* \* \* \*